United States Patent
Filipovic et al.

(10) Patent No.: US 10,576,451 B2
(45) Date of Patent: Mar. 3, 2020

(54) SYSTEMS AND METHODS FOR GAS TREATMENT

(71) Applicant: BLUE-ZONE TECHNOLOGIES LTD., Concord (CA)

(72) Inventors: Dusanka Filipovic, Toronto (CA); Laurence Whitby, Victoria Harbour (CA); Biljana Bicky Milin, Etobicoke (CA); Frederick Cashin, Brooklyn (CA)

(*) Notice: Subject to any disclaimer, the term of this patent is extended or adjusted under 35 U.S.C. 154(b) by 0 days.

(21) Appl. No.: 14/966,520

(22) Filed: Dec. 11, 2015

(65) Prior Publication Data

US 2016/0096793 A1 Apr. 7, 2016

Related U.S. Application Data

(62) Division of application No. 14/717,217, filed on May 20, 2015, now Pat. No. 9,314,766, which is a division
(Continued)

(51) Int. Cl.
*B01D 53/02* (2006.01)
*B01J 20/20* (2006.01)
(Continued)

(52) U.S. Cl.
CPC ............ *B01J 20/20* (2013.01); *A61M 16/009* (2013.01); *A61M 16/0093* (2014.02);
(Continued)

(58) Field of Classification Search
CPC ............ A61M 16/009; A61M 16/0093; A61M 16/1055; A61M 16/1065; A61M 2205/84;
(Continued)

(56) References Cited

U.S. PATENT DOCUMENTS

| 4,061,724 A | 12/1977 | Grose et al. |
| 4,755,439 A * | 7/1988 | Trocciola .......... H01M 8/04089 429/415 |

(Continued)

FOREIGN PATENT DOCUMENTS

| CA | 1339833 | 4/1998 |
| CA | 2423367 | 4/2002 |

(Continued)

OTHER PUBLICATIONS

Canadian Intellectual Property Office, International Search Report and Written Opinion on PCT Appln. No. PCT/CA2010/001366, dated Jan. 13, 2011.
(Continued)

*Primary Examiner* — Christopher P Jones
(74) *Attorney, Agent, or Firm* — Gowling WLG (Canada) LLP; Neil W. Henderson

(57) ABSTRACT

A system and process for the recovery of at least one halogenated hydrocarbon from a gas stream. The recovery includes adsorption by exposing the gas stream to an adsorbent with a lattice structure having pore diameters with an average pore opening of between about 5 and about 50 angstroms. The adsorbent is then regenerated by exposing the adsorbent to a purge gas under conditions which efficiently desorb the at least one adsorbed halogenated hydrocarbon from the adsorbent. The at least one halogenated hydrocarbon (and impurities or reaction products) can be condensed from the purge gas and subjected to fractional distillation to provide a recovered halogenated hydrocarbon.

2 Claims, 10 Drawing Sheets

Related U.S. Application Data of application No. 13/393,692, filed as application No. PCT/CA2010/001366 on Aug. 31, 2010, now Pat. No. 9,039,808.

(60) Provisional application No. 61/239,051, filed on Sep. 1, 2009.

(51) Int. Cl.

| | | |
|---|---|---|
| *A61M 16/00* | (2006.01) | |
| *B01D 53/70* | (2006.01) | |
| *B01J 20/10* | (2006.01) | |
| *B01J 20/12* | (2006.01) | |
| *B01J 20/16* | (2006.01) | |
| *B01J 20/18* | (2006.01) | |
| *B01J 20/28* | (2006.01) | |
| *B01J 20/34* | (2006.01) | |
| *C07C 41/34* | (2006.01) | |
| *F16K 11/00* | (2006.01) | |
| *G01N 25/18* | (2006.01) | |
| *G01N 27/14* | (2006.01) | |
| *A61M 16/10* | (2006.01) | |

(52) U.S. Cl.
CPC ............ *B01D 53/02* (2013.01); *B01D 53/70* (2013.01); *B01J 20/103* (2013.01); *B01J 20/12* (2013.01); *B01J 20/16* (2013.01); *B01J 20/18* (2013.01); *B01J 20/2808* (2013.01); *B01J 20/28057* (2013.01); *B01J 20/28061* (2013.01); *B01J 20/28064* (2013.01); *B01J 20/28071* (2013.01); *B01J 20/28078* (2013.01); *B01J 20/28083* (2013.01); *B01J 20/3408* (2013.01); *B01J 20/3483* (2013.01); *C07C 41/34* (2013.01); *F16K 11/00* (2013.01); *G01N 25/18* (2013.01); *G01N 27/14* (2013.01); *A61M 16/1055* (2013.01); *A61M 16/1065* (2014.02); *A61M 2205/84* (2013.01); *B01D 2253/1085* (2013.01); *B01D 2253/306* (2013.01); *B01D 2253/308* (2013.01); *B01D 2257/2062* (2013.01); *B01D 2257/2064* (2013.01); *B01D 2257/2066* (2013.01); *B01D 2257/504* (2013.01); *B01D 2258/02* (2013.01); *B01D 2259/4009* (2013.01); *B01D 2259/40094* (2013.01); *B01D 2259/4533* (2013.01); *B01J 2220/603* (2013.01); *B01J 2220/606* (2013.01); *Y02C 10/08* (2013.01)

(58) Field of Classification Search
CPC ...... B01D 2253/1085; B01D 2253/306; B01D 2253/308; B01D 2257/2062; B01D 2257/2064; B01D 2257/2066; B01D 2257/504; B01D 2258/02; B01D 2259/4009; B01D 2259/40094; B01D 2259/4533; B01D 53/02; B01D 53/70; B01J 20/103; B01J 20/12; B01J 20/16; B01J 20/18; B01J 20/20; B01J 20/28057; B01J 20/28061; B01J 20/28064; B01J 20/28071; B01J 20/28078; B01J 20/2808; B01J 20/28083; B01J 20/3408; B01J 20/3483; B01J 2220/603; B01J 2220/606; C07C 41/34; F16K 11/00; G01N 25/18; G01N 27/14; Y02C 10/08
See application file for complete search history.

(56) References Cited

U.S. PATENT DOCUMENTS

| | | | |
|---|---|---|---|
| 4,829,810 A * | 5/1989 | Anderson | ............ G01N 27/18 338/34 |
| 5,044,363 A | 9/1991 | Burkhart | |
| 5,125,221 A | 6/1992 | Patil et al. | |
| 5,231,980 A | 8/1993 | Filipovic et al. | |
| 5,417,742 A | 5/1995 | Tamhankar et al. | |
| 5,447,701 A | 9/1995 | Inoue et al. | |
| 5,515,845 A | 5/1996 | Filipovic et al. | |
| 5,520,169 A | 5/1996 | Georgieff et al. | |
| 5,928,411 A | 7/1999 | Falb et al. | |
| 6,134,914 A | 10/2000 | Eschwey et al. | |
| 6,405,539 B1 | 6/2002 | Stach et al. | |
| 2,729,329 A1 | 5/2004 | Berry | |
| 2005/0155380 A1 | 7/2005 | Rock | |
| 2006/0254587 A1 | 11/2006 | Berry et al. | |
| 2006/0254589 A1 | 11/2006 | Berry et al. | |
| 2006/0254590 A1 | 11/2006 | Berry et al. | |
| 2008/0214875 A1 | 9/2008 | Jones et al. | |
| 2013/0220330 A1 * | 8/2013 | Hunt | ..................... A61M 16/01 128/205.27 |

FOREIGN PATENT DOCUMENTS

| | | |
|---|---|---|
| CA | 2514236 | 9/2004 |
| CA | 2756187 | 8/2011 |
| CN | 88101700 | 10/1988 |
| CN | 1462206 | 12/2003 |
| DE | 4208521 | 9/1993 |
| DE | 19749963 | 5/1999 |
| EP | 0284227 | 9/1988 |
| EP | 1155729 | 11/2001 |
| JP | 61-068536 | 4/1986 |
| JP | 63-315127 | 12/1988 |
| JP | 2002172171 | 6/2002 |
| JP | 2009-160559 | 7/2009 |
| WO | 2005099797 | 10/2005 |
| WO | 2007019161 | 2/2007 |
| WO | 2009083275 | 7/2009 |
| WO | 20090085247 | 7/2009 |

OTHER PUBLICATIONS

State Intellectual Property Office of China, First Office Action on Chinese Patent Appln. No. 201080044151.7, dated Jun. 13, 2013.
State Intellectual Property Office of China, Second Office Action on Chinese Patent Appln. No. 201080044151.7, dated Mar. 7, 2014.
Japan Patent Office, Notification of Reasons for Refusal on Japanese Patent Appln. No. 2002-527167, dated Jul. 22, 2014.
United States Patent and Trademark Office, Office Action on U.S. Appl. No. 13/393,692, dated Jul. 9, 2014.
ISA/CA Canadian Intellectual Property Office, Invitation to Pay Additional Fees dated Nov. 5, 2010, PCT Application No. CA2010/001366, Quebec, Canada.
Australian Patent Office, Examination Report No. 1 on Australian App No. 2010291823, dated Dec. 10, 2015.
Canadian Intellectual Property Office, Office Action on Canadian App No. 2,772,776, dated May 26, 2016.
Australian Patent Office, Examination Report No. 2 on Australian App No. 2010291823, dated Jun. 21, 2016.
Canadian Intellectual Patent Office, Office Action on Canadian App No. 2,772,776, dated Jul. 12, 2016.
Canadian Intellectual Patent Office, Notice of Allowance on Canadian App No. 2,772,776, dated Sep. 1, 2016.
European Patent Office, Search Report on European Patent Appln. No. 10813202.8, dated Dec. 19, 2016.
European Patent Office, Partial Search on European Patent Appln. No. 10813202, dated Sep. 12, 2016.
Official Action on corresponding CN patent application No. 201610019342.7, dated Oct. 10, 2017.
Official Action on corresponding CN patent application No. 201610019342.7, dated Aug. 8, 2018.

(56) References Cited

OTHER PUBLICATIONS

Official Action on corresponding CN patent application No. 201610019342.7, dated Apr. 22, 2019.
Official Action on corresponding EP patent application No. 10813202.8, dated Jul. 27, 2018.
Official Action on corresponding ID patent application No. W00201201224, dated Dec. 5, 2017.
Official Action on corresponding IN patent application No. 2769/DELNP/2012, dated Sep. 19, 2017.
Official Action on corresponding JP patent application No. 2016-019622, dated Dec. 20, 2016.
Official Action on corresponding JP patent application No. 2016-019622, dated Oct. 10, 2017.
Official Action on corresponding JP patent application No. 2016-019622, dated Aug. 28, 2018.
J-PlatPat, English translation of Abstract of JP 61-068536, Apr. 8, 1986.
Espacenet, English translation of Abstract of CN 88101700, Oct. 5, 1988.
Espacenet, English translation of Abstract of JP 63-315127, Dec. 22, 1988.
J-PlatPat, English translation of Abstract of JP 2009-160559, Jul. 23, 2009.

* cited by examiner

SYSTEMS AND METHODS FOR GAS TREATMENT

CROSS REFERENCE TO RELATED APPLICATIONS

This application is a division of U.S. patent application Ser. No. 14/717,217, filed May 20, 2015, which is itself a division of U.S. patent application Ser. No. 13/393,692, filed May 18, 2012 (now U.S. Pat. No. 9,039,808, issued May 26, 2015), which is a national phase of International Application No. PCT/CA2010/001366, filed Aug. 31, 2010, which claims the benefit of U.S. Provisional Patent Application No. 61/239,051, filed Sep. 1, 2009, all of which are incorporated herein by reference in their entirety.

FIELD

The present application relates generally to the recovery of halogenated hydrocarbons from a gas stream. Generally speaking the recovery is for the purpose of the extension of their life cycle or disposal. More particularly, the present application relates to the recovery from a gas stream by adsorption; subsequent desorption and recovery from the desorption gas by condensation; and subsequent separation and purification by fractional distillation of halogenated hydrocarbon inhalation anesthetics.

BACKGROUND

Halogenated hydrocarbon compounds include the families of compounds: bromo-, fluoro- and/or chloro-ethers, fluorinated alkyl ethers, chlorofluorocarbons and chlorofluoro ethers and their derivatives. These families of compounds are typically used as solvents, refrigerants, anesthetics, aerosol propellants, blowing agents and the like. Many of these compounds are widely used and are routinely discharged into the atmosphere. Particularly in the case of medical anesthetic gases, if these compounds could be recovered, retrieved and purified to medical standards there would be a considerable cost saving and reduction in environmental pollution. In view of the possible negative effects of halogenated hydrocarbons that are released into the atmosphere, attempts have already been made to recover such gases.

In view of the rising costs of the inhalation anesthetics and the environmental effects (e.g. toxic greenhouse and ozone depletion) of the drugs, attempts are being made to recover the inhalation anesthetics before the anesthetics are discharged into the atmosphere. A system can be provided for recovering inhalation anesthetics from gas streams exiting anesthetic gas machines (which may include patient exhalent following administration to a patient) by capturing scavenged gas containing the anesthetic rich gas stream, removing water vapor and then extracting the anesthetic using either a cryogenic process in which the vapors of the anesthetics are condensed to liquid phase, or an adsorbent material which is processed later to remove the anesthetics. The collected liquid anesthetics can then be reintroduced directly into an anesthetic gas machine. Such approach has little if any facility to control bacterial contamination and potentially recycles harmful microorganisms to another patient or the anesthetic gas machine in general. Additionally, there is no assurance that the condensed drugs are separated into individual components and that each recycled drug meets the appropriate medical standards and regulations.

In another approach for recovering inhalation anesthetics, an adsorbent material in an appropriate container is used to adsorb the inhalation anesthetics from the gas stream exiting the anesthetic gas machine. When the adsorbent material is saturated, the container is removed and placed in a regeneration system. A purging gas, such as steam, is used to remove the anesthetics from the adsorbent material. The purged gas is then collected, water is removed therefrom, and the anesthetics are condensed and subjected to fractionation to separate out the individual anesthetics. Such an approach can be difficult as steam, having an elevated temperature, can cause catalytic reactions with the adsorbent and adsorbate leading to a product breakdown and pure yields of the recovered anesthetics. Furthermore, such an approach can be difficult because a number of different inhalation anesthetics may be used in one operating room and each inhalation anesthetic may require different adsorbents and differing desorption requirements. Further, methods of separating a number of different inhalation anesthetics can be very complex due to differing chemistries and the potential for impurities, including by-products, in the combined materials.

Examples of anesthetics which can be captured are sold under the trade-marks ETHRANE and FORANE, and are disclosed in U.S. Pat. Nos. 3,469,011; 3,527,813; 3,535,388; and 3,535,425. The respective chemical formulae for these anesthetics are: 1,1,2-trifluoro-2-chloroethyl difluoromethyl ether and 1-chloro-2,2,2-trifluoroethyl difluoromethyl ether. These chemicals are also commonly known as "enflurane" and "isoflurane", respectively.

Other anesthetics of particular importance are sold under the trade-marks SUPRANE and ULTANE, and are disclosed in U.S. Pat. Nos. 3,897,502; 4,762,856; and 3,683,092. The respective chemical formulae for these anesthetics are: 2,2,2-trifluoro-1-fluoroethyl-difluoromethyl ether and 2,2,2-trifluoro-1-[trifluoromethyl]ethyl fluoromethyl ether. These chemicals are commonly known as "desflurane" and "sevoflurane", respectively. They are highly volatile organic compounds, produced in a liquid form and then evaporated and mixed with other carrier medical gases, such as nitrous oxide, oxygen and/or medical air in the anesthetic gas machine before administered to a patient to be used as an inhalation anesthetic. The gas stream exiting the anesthetic gas machine is rich with inhalation anesthetics and contains entrained $CO_2$ and moisture and possibly some by-products that potentially result from the anesthetic gas mix recirculation stream passing over soda lime absorbent in the patient breathing circuit.

While there may be methods and systems for adsorbing some of these anesthetics individually or for purifying some of these chemicals individually to a level for medical use, effective methods and systems of selective recovering anesthetics or a mixture of anesthetics from a gas stream, for separating the anesthetics, if necessary, and for purifying the anesthetics would be economically advantageous.

It is, therefore, desirable to provide a system and method for at least some of capturing, recovering, retrieving, separating and purifying a variety of inhalation anesthetics such as desflurane and/or sevoflurane from a gas stream that overcomes at least some of the problems with conventional systems. It would be similarly desirable to provide a system and method for at least some of capturing, recovering, separating and purifying halogenated hydrocarbons generally.

SUMMARY

In one aspect of the application, described in more detail below, there is provided a process for the recovery of at least one halogenated hydrocarbon from a gas stream, the process comprising: exposing the gas stream to an adsorbent with a lattice structure having pore diameters large enough to permit molecules of the at least one halogenated hydrocarbon to enter and be adsorbed in internal cavities of the adsorbent lattice, the adsorbent having a pore lattice structure with an average pore opening of between about 5 and about 50 angstroms; removing from the gas stream the adsorbent containing the adsorbed at least one halogenated hydrocarbon; and regenerating the adsorbent with a purge gas by exposing the adsorbent to the purge gas under conditions which efficiently desorb the at least one adsorbed halogenated hydrocarbon from the adsorbent. In particular, the process is intended to operate without causing catalytic reaction; without adsorbate breakdown and with high yields.

In some cases, the average pore opening is between about 5 and about 10 angstroms. In other cases, the average pore opening is between about 15 and about 30 angstroms. The adsorbent can be a $SiO_2$ based organophilic material having a $SiO_2$ content of 90 wt % or greater. The adsorbent can be less than 10% by weight of $Al_2O_3$. The adsorbent can be substantially free of $Al_2O_3$. The adsorbent can have a weight ratio of $SiO_2:Al_2O_3$ of 98:1 or greater. The adsorbent can have less than about 1% by mass of cation. The adsorbent can have a neutral surface. The adsorbent can have a specific surface area of about 400 to about 1500 $m^2/g$. The adsorbent can have a specific surface area of about 500 to about 1250 $m^2/g$. The adsorbent can have a specific surface area of about 600 to about 900 $m^2/g$. The adsorbent can have average pore size of 20 angstroms, and/or a surface area of 750 $m^2/g$.

During the process, the adsorbent can be exposed to the gas stream until at least just prior to the adsorbent being saturated. In other cases the adsorbent can be exposed until after being saturated.

The at least one halogenated hydrocarbon can be removed from the purge gas by condensing the at least one halogenated hydrocarbon. The at least one halogenated hydrocarbon can be an inhalation anesthetic. The anesthetic can be sevoflurane, desflurane, halothane, isoflurane or enflurane. The at least one halogenated hydrocarbon can be a bromochlorofluoro ether, a fluorinated alkyl ether, a chlorofluorocarbon, a chlorofluoro ether, or one of their derivatives.

The gas stream can be a gas stream exiting an anesthetic gas machine, a gas stream of a patient breathing circuit within an anesthetic gas machine, or a gas stream associated with a hospital's central collection system for the hospital's anesthetic gas machines' exhaust streams. The anesthetics in the gas stream can be selectively adsorbed on the adsorbent material; and the anesthetics adsorbed on the adsorbent material can be desorbed from the adsorbent material, condensed, separated and each purified to medical standards.

Exposing the gas stream to the adsorbent can comprise passing the gas stream through a bed of the adsorbent contained in a canister. Exposing the gas stream to the adsorbent can comprise passing the gas stream through a bed of the adsorbent contained in a central collector or a canister, which is capable of adsorbing halogenated hydrocarbons from multiple gas streams, such as the gas stream from the hospital central anesthetic gas machines' gas disposal pipe.

The process can further comprise: detecting the at least one halogenated hydrocarbon exiting the bed of adsorbent, actuating a detectable alarm to indicate that the bed of adsorbent is saturated, and replacing the saturated adsorbent with unsaturated adsorbent. The saturated adsorbent can be heated to an elevated temperature at controlled process conditions during regeneration of the adsorbent to assist in desorption of the at least one halogenated hydrocarbon from the adsorbent. The saturated adsorbent can be heated with microwaves. A purge gas can be heated prior to being fed through or passed through the saturated adsorbent to raise the temperature of the saturated adsorbent to the elevated temperature. The elevated temperature can be in the range of 30° C. to 220° C. In some cases, the elevated temperature can be between 30° C. and 180° C. The purge gas can be heated to a temperature in the range of 30° C. to 220° C. In some cases, the purge gas can be heated to a temperature between 30° C. and 180° C. The purge gas can be an inert gas such as nitrogen.

The at least one halogenated hydrocarbon can be a mixture of at least two different anesthetics, the adsorbent can be configured to adsorb the at least two different anesthetics, the purge gas can desorb the at least two different anesthetics from the adsorbent into the purge gas, and where the process can further comprise: condensing the two different anesthetics desorbed into the purge stream into liquid form, and purifying the condensed liquid form of the two different anesthetics by fractional distillation to isolate and separate purified, anesthetics. The fractional distillation can be performed under either vacuum or pressure. The process can further comprise washing the condensed liquid that is a mixture of different anesthetics with water before purification by fractional distillation.

The mixture of the at least two different anesthetics purified by fractional distillation can comprise 2,2,2-trifluoro-1-fluoroethyl-difluoromethyl ether and 2,2,2-trifluoro-1-[trifluoromethyl]ethyl fluoromethyl ether.

In a further aspect, there is provided a use of an adsorbent having a pore lattice structure with an average pore opening between about 5 and about 50 angstroms for the adsorption of an inhalation anesthetic. The inhalation anesthetic can be 2,2,2-trifluoro-1-fluoroethyl-difluoromethyl ether or 2,2,2-trifluoro-1-[trifluoromethyl]ethyl fluoromethyl ether. In some cases, the average pore opening is between about 5 and about 10 angstroms. In other cases, the average pore opening is between about 15 and about 30 angstroms. The adsorbent can be a $SiO_2$ based organophilic material having a $SiO_2$ content of 90 wt % or greater. The adsorbent can have less than 10% by weight of $Al_2O_3$. The adsorbent can be substantially free of $Al_2O_3$. The adsorbent can have a weight ratio of $SiO_2:Al_2O_3$ of 98:1 or greater. The adsorbent can have less than about 1% by mass of cation. The adsorbent can have a neutral surface. The adsorbent can have a specific surface area of about 400 to about 1500 $m^2/g$. The adsorbent can have a specific surface area of about 500 to about 1250 $m^2/g$. The adsorbent can have a specific surface area of about 600 to about 900 $m^2/g$. The adsorbent can have average pore size of 20 angstroms, and/or a surface area of 750 $m^2/g$.

In a further aspect, there is provided an adsorbent for adsorbing a halogenated hydrocarbon, the adsorbent having a pore lattice structure with an average pore opening between about 5 and about 50 angstroms, less than 10% by weight of cation; and a surface area of between about 400 $m^2/g$ and about 1500 $m^2/g$. In some cases, the adsorbent has an average pore opening between about 5 and about 10 angstroms. In other cases, the average pore opening is between about 15 and about 30 angstroms. The adsorbent can be a $SiO_2$ based organophilic material having a $SiO_2$ content of 90 wt % or greater. The adsorbent can have less than 10% by weight of $Al_2O_3$. The adsorbent can be substantially free of $Al_2O_3$. The adsorbent can have a weight ratio of $SiO_2:Al_2O_3$ of 98:1 or greater. The adsorbent can have less than about 1% by mass of cation. The adsorbent can have a neutral surface. The adsorbent can have a specific surface area of about 400 to about 1500 $m^2/g$. The adsorbent can have a specific surface area of about 500 to about 1250 m²/g. The adsorbent can have a specific surface area of about 600 to about 900 m²/g. The adsorbent can have average pore size of 20 angstroms, and/or a surface area of 750 m²/g.

In a further aspect, there is provided an adsorbent system for adsorbing halogenated hydrocarbons, the adsorbent system comprising: one adsorbent having a pore lattice structure with an average pore opening of between about 5 angstroms and about 10 angstroms; less than 10% w/w of $Al_2O_3$, a surface area of between about 400 m²/g and about 1500 m²/g; and another adsorbent having a pore lattice structure with an average pore opening of between about 15 angstroms and about 30 angstroms; less than 10% w/w $Al_2O_3$, surface area of between about 400 m²/g and 1500 m²/g.

In a further aspect, there is provided a sensor for detecting the presence of halogenated hydrocarbons in a gas stream, the sensor comprising: an electrical current generator for passing a current through the gas stream; a conductivity sensor for determining the thermal conductivity of the gas stream based on the current passing through the gas stream; a processor for comparing the thermal conductivity with predetermined values to determine if halogenated hydrocarbons are present in the gas stream.

In a further aspect, there is provided an adsorbent system for adsorbing anesthetics, the adsorbent system comprising: an input for receiving a gas stream containing the anesthetics from an operating room exhaust or the hospital central anesthetic gas exhaust; a non-chemical dryer connected to the input; a chemical dryer connected to the non-chemical dryer; a filter connected to the chemical dryer for removing bacterial and particulate matter; and an adsorber unit connected to the filter for adsorbing the anesthetics from the gas stream.

DESCRIPTION OF THE FIGURES

Other aspects and features of the present application will become apparent to those ordinarily skilled in the art upon review of the following description of specific embodiments in conjunction with the accompanying figures.

Embodiments will now be described, by way of example only, with reference to the attached Figures, wherein.

DETAILED DESCRIPTION

Generally, the present application relates to methods and systems for capturing a variety of halogenated hydrocarbons and for purifying the captured compounds. Compounds generally known as halogenated hydrocarbons include bromo-, chloro- and/or fluoro-ethers, fluorinated alkyl ethers, chloro-fluorohydrocarbons, chlorofluoroethers and their derivatives.

Inhalation anesthetics are well known types of halogenated hydrocarbons which include isoflurane (Forane™), enflurane (Enthrane™), halothane (Halothane™) methoxyflurane (Penthrane™), desflurane (Suprane™) and sevoflurane (Ultane™).

Other well known halogenated hydrocarbons include the variety of refridgerant gases, such as Freons™ (which include trichlorofluromethane, and dichlorodifluoromethane). This family of halogenated hydrocarbon compounds includes, for example, an alkyl group or ether group substituted with one or more of chloro-, fluoro- and bromogroups.

While the following description relates to the recovery of various inhalation anesthetics, it is appreciated that the principles of the application, which are demonstrated by the following embodiments, can be equally applicable to the recovery of other types of halogenated hydrocarbons.

During surgery, a patient is treated with inhalation anesthetics by way of an anesthetic gas machine. It is appreciated that the use of the term "patient" is in a general sense and should not be limited to human patients. It is understood that anesthesia is practiced on a variety of mammals, not only humans, but also animals such as horses, cattle and other forms of livestock, domestic pets and the like.

The inhalation anesthetics are first partly evaporated in the vaporizer of the anesthetic gas machine and typically delivered in combination with "medical air", which is typically a combination of oxygen and/or nitrous oxide and/or air. As the patient breathes the gas stream containing the anesthetic (with support of a respirator), a desired degree of unconsciousness is achieved and monitored by the anesthetist. Typically, not all of the anesthetic is adsorbed or metabolized by the patient. Flow rates of the gas stream to the patient may be in the range of 0.5 to 7 liters per minute, where the concentration by volume of the anesthetic may be in the range of 0% to 8.5% depending on numerous factors and conditions evaluated and monitored by the anesthetist.

It is important to ensure that the gas mixture containing anesthetic being administered by the anesthetic gas machine is not exhausted into the operating theatre, because exposure to the anesthetics can have both short term and long term effects on the people in the operating room. As such, scavenging systems are typically provided to contain the anesthetic rich gases (which may include patient exhalent) and/or externally divert the anesthetic rich gases outside of the operating room. In the present embodiments, the anesthetic rich gas is adsorbed on an adsorbent before the gas is vented to the atmosphere.

Figure 1:
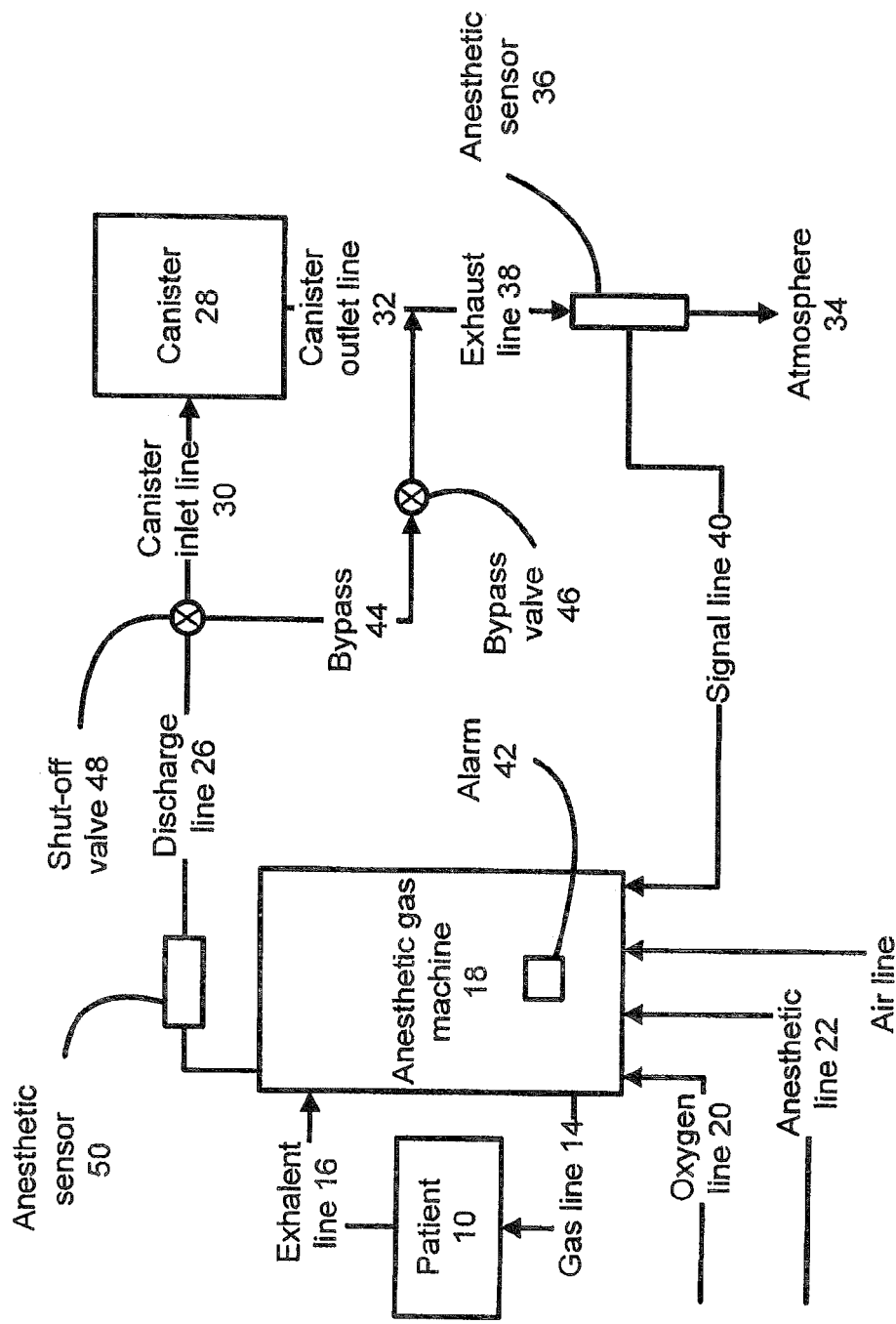
FIG. 1 is a schematic of a system for capturing anesthetics from a gas stream exiting an anesthetic gas machine.

In one embodiment of a collection system herein, the collection may be performed using an container collection system. A container collection system is understood to be a collection system where one or more canisters are used to collect anesthetics from a single anesthetic gas machine or from multiple anesthetic gas machines. One embodiment of a container collection system is illustrated in FIG. 1 where a single canister is in line with the outlet of the anesthetic gas machine. In this system the patient represented at 10 is connected to a mask (not shown) having a gas line 14 communicating therewith. The desired mixture of anesthetic and carrier gas or gases is delivered in gas line 14 to the patient 10. The anesthetic rich gas is returned in exhalent line 16 to the anesthetic gas machine 18. The anesthetic gas machine 18, which is supplied with an anesthetic and carrier gases (for example medical air—in this example, oxygen and air) in oxygen line 20, anesthetic line 22 and air line 24, is operated to introduce the desired mixture in gas line 14. The anesthetic rich gas in exhalent line 16 is discharged from the anesthetic gas machine 18 via discharge line 26. A canister 28, having an inlet line 30 and an outlet line 32, is interposed in discharge line 26 at a position outside of a patient breathing circuit. The anesthetic rich gas in discharge line 26, therefore, flows through the canister 28 before ultimately exhausting to atmosphere 34. With some anesthetic gas machines, the patient breathing circuit can be open, semiclosed or closed. An open circuit results in no rebreathing by the patient of the gas returned to the anesthetic gas machine via exhalent line 16. A semiclosed circuit results in partial rebreathing by the patient of the gas returned to the anesthetic gas machine via exhalent line 16. A closed circuit results in complete rebreathing by the patient of the gas returned to the anesthetic gas machine via exhalent line 16. Anesthetic gas machines with semiclosed or closed circuits can use a $CO_2$ absorber to scrub the patient's exhaled carbon dioxide.

The canister 28 is charged with an adsorbent that adsorbs the anesthetic from the gas stream exiting the anesthetic gas machine, intending to leave the stream discharge to atmosphere 34 substantially free of inhalation anesthetic. An anesthetic sensor 36 may be provided in exhaust line 38 to sense the presence of anesthetics exiting from the canister 28. It is appreciated that an adsorption front of adsorbed anesthetics travels along the bed of adsorbent towards the canister outlet as the anesthetic is adsorbed. Such an adsorption front will usually have a curved profile across the canister as it approaches the outlet. The sensor would sense when any portion of the adsorption front has broken through the adsorbent into the outlet. Replacement of the canister may be desirable at this time even though the bed of adsorbent may not be fully saturated with anesthetic. The anesthetic sensor 36 may be connected via a signal line 40 to the anesthetic gas machine 18, or to some remote monitoring station (not shown). The anesthetic gas machine 18 or remote monitoring station may be equipped with an alarm 42 which is actuated when the anesthetic sensor 36 senses anesthetics in exhaust line 38. The alarm can be a light and/or audible alarm. This would indicate to the anesthetist or a technician that the canister 28 should be replaced so that continued recovery of anesthetics is achieved. It is appreciated that a bypass 44 controlled by a bypass valve 46 may be provided to route the gas stream exiting the anesthetic gas machine 18 past the canister 28 during replacement of the canister. In this instance, a shut-off valve 48 is provided in discharge line 26 to shut off the supply to canister 28 during replacement of the canister. Instead of bypass 44 and shut-off valve 48, a three-port valve could direct the flow of gas past the canister 28 during replacement of the canister.

There may be cases where the medical air supply may be left on even though no anesthetic is being used. In such a situation, it is undesirable to continue to flow medical air through the canister since the continuous flow of medical air can slowly desorb the anesthetics previously captured. In order to address such a situation, a second anesthetic sensor 50 may be provided in discharge line 26 in order to detect anesthetics. In the event that no anesthetics in the flow are detected by the anesthetic sensor 50, bypass 44, controlled by bypass valve 46, could be triggered to route the medical air directly to the atmosphere at 34.

As discussed above, anesthetic gas machines can include partially closed or closed breathing circuits. In such breathing circuits, patient exhalent is circulated through the breathing circuit via a ventilator and is scrubbed to remove exhaled carbon dioxide before being re-breathed by the patient. In an alternative collection system, termed an "breathing circuit collection system", the anesthetics are adsorbed by a canister in-line with the breathing circuit. The canister of this embodiment is positioned to adsorb anesthetic gas before the anesthetic gas machine discharges the exhaust gas to atmosphere.

Figure 2:
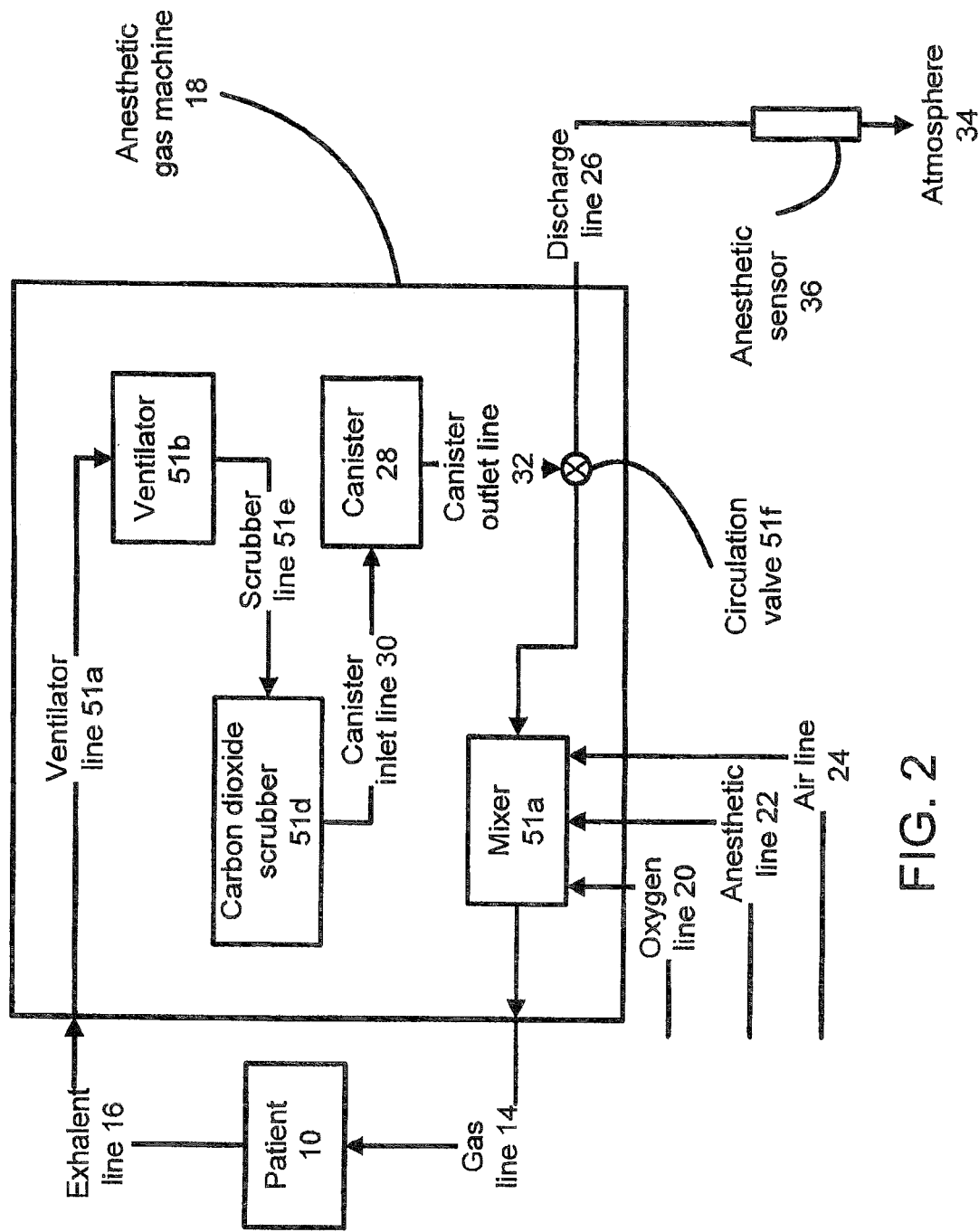
FIG. 2 is a schematic of a system for capturing anesthetics from a gas stream within a patient breathing circuit of an anesthetic gas machine.

As illustrated in FIG. 2, the anesthetic gas machine 18 accepts an anesthetic and carrier gases (for example medical air—in this example, oxygen and air) in oxygen line 20, anesthetic line 22 and air line 24. These are mixed in mixer 51a. The anesthetic rich gas is delivered to patient 10 via gas line 14. Patient exhalent is returned to the anesthetic gas machine 18 via patient exhalent line 16. The returned gas is delivered to ventilator 51b via ventilator line 51c. The anesthetic rich gas is delivered to carbon dioxide scrubber 51d via scrubber line 51e and scrubbed of carbon dioxide. The scrubbed gas is delivered to canister 28 via canister inlet line 30. The canister 28 is charged with an adsorbent that adsorbs the anesthetic from the gas stream exiting the carbon dioxide scrubber 51d.

Although FIG. 2 illustrates the canister 28 as being positioned after the ventilator 51b and scrubber 51d, it should be understood that the relative positions of the ventilator, scrubber and canister along the breathing circuit could be changed.

The gas flowing out of canister outlet 32 is directed via a circulation valve 51f either back to the mixer 51a or, via discharge line 26, out of the anesthetic gas machine 18 and ultimately to atmosphere 34. An anesthetic sensor 36 may be provided in discharge line 26 to sense the presence of anesthetics exiting the anesthetic gas machine 18. Sensors and valves, such as those described above with regard to the container collection system, could be used to determine when the canister needs to be replaced and to direct the flow of gas around the canister during replacement of the canister.

Figure 3:
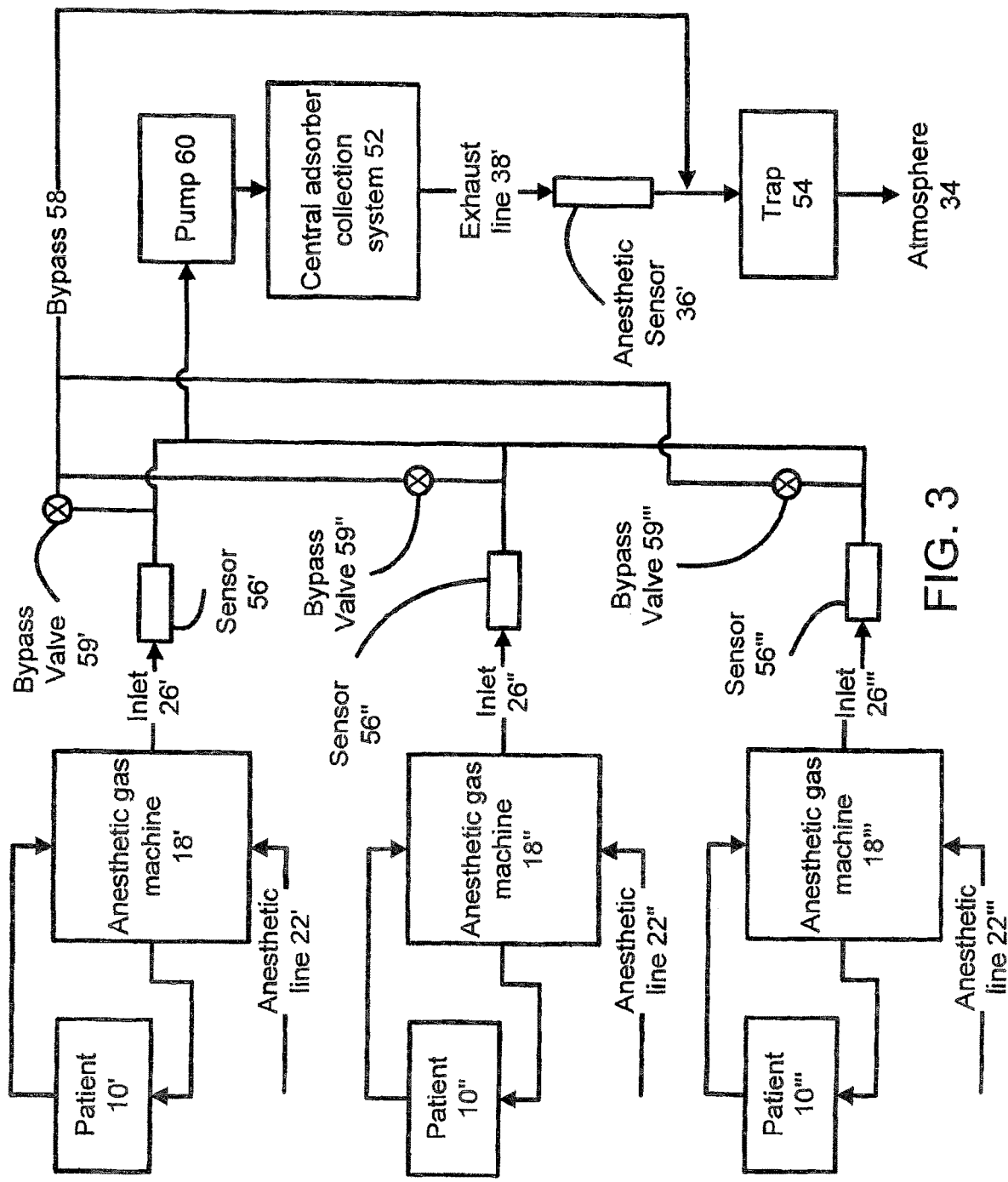
FIG. 3 is a schematic of a central collection system for capturing anesthetics from multiple anesthetic gas machines or a hospital central anesthetic gas exhaust.

In an alternative system, illustrated in FIG. 3, the anesthetics are captured by a central adsorber collection system 52. A central adsorber collection system is understood to be a collection system that takes as its input anesthetics from multiple anesthetic gas machines (e.g. 18', 18" and 18'''), which may be located in multiple operating rooms. This central collection system would operate in a similar fashion to the container collection system described above, in that the central adsorber collection system would be charged with at least one adsorbent which selectively adsorbs the anesthetics from the combined gas streams exiting the anesthetic gas machines, intending to leave the discharge stream substantially free of anesthetics for ultimately exhausting to atmosphere 34. The central adsorber collection system may include several adsorbers and each geometrically sized to facilitate larger volume of adsorbate in the system and/or less frequent replacements and/or desired longer adsorption time.

An anesthetic sensor 36' may be provided in the central adsorber collection system exhaust line 38' to sense the presence of anesthetics exiting the central adsorber collection system. The anesthetic sensor 36' would sense when anesthetics have broken through the adsorbent into the exhaust and prompt a user with feedback (e.g. an alarm) to change the adsorbent by, for instance, replacing one or more adsorbers, replacing the adsorbent in one or more adsorbers, or regenerating the adsorbent. Trap 54 may be provided in the exhaust line 38', located before the system exhausts to the atmosphere 34, in order to reduce the possibility that anesthetics are released to the atmosphere. The trap 54 may have the same adsorbent as the central adsorber collector, or may have a different adsorbent, such as activated carbon, silicalite, or molecular sieves.

An alternative to providing the anesthetic sensor 36' for sensing an anesthetic in the exhaust line is to provide a weight sensor (e.g. a load cell) such that the weight of the capture device (or adsorbent or canisters) could be monitored and the user could be prompted to change or regenerate the adsorbent once a predetermined weight of anesthetic was collected in the central adsorber collection system.

In another alternative to using the anesthetic sensor 36', historical loading patterns could be used to determine an appropriate time to change or regenerate the adsorbent or to determine an appropriate adsorber size to support a given time of collection. Replacement or regeneration of the adsorbent in any of the above alternatives may be desirable even though the adsorbent is not fully saturated with anesthetic.

Sensors 56', 56" and 56'" may be provided in central adsorber collection system inlet lines 26', 26" and 26'". The sensor 56', 56" and 56'" sense the presence of anesthetics in the medical air and/or operation of the anesthetic gas machine. In cases where no anesthetics are detected, or if the associated anesthetic gas machine is not in operation, inlet lines 26', 26" and/or 26'" may be closed off to isolate the appropriate operating room from the central adsorber collection system 52. The inlet lines 26', 26" and 26'" may alternatively be used to route the medical air, via bypass 58, to the atmosphere and away from the central collection system 52. Closing off the inlet lines 26', 26" and 26'" or routing the medical air through bypass 58 can be achieved using bypass valves 59', 59" and 59'".

One example of such a sensor is a sensor which can be used to detect anesthetics in the exhaust line. Such a sensor could measure thermal conductivity of the gas in the exhaust line and transform the thermal variations into an electrical signal. Thermal conductivity of the gas stream with anesthetic is a physical property found to vary under normal operating conditions of the anesthetic gas machine. Such a signal could be used to provide a numerical indication of the concentration of anesthetic in the exhaust line. As described above, the signal could also be used to operate a valve to isolate the operating room or to route the medical air to the atmosphere. Another example of an appropriate sensor would be a pressure sensor or valve which would detect pressure coming from the anesthetic gas machine.

One of the issues involved in a central adsorber collection system relates to the flow rate and concentration of anesthetics in the flow. Typically, a hospital scavenging system uses a pump or blower device 60 located before the central collection system to draw the gas stream from various operating rooms into the scavenging system. This device draws the gas stream originating from the anesthetic gas machines 18', 18" and 18'", as well as additional "make up" air. An increased flow rate due to the make up air results in a dilution of the concentration of anesthetics 22', 22" and 22'". This dilution can be, for example, in the range of 1:20 (volume of anesthetic gas stream from the anesthetic gas machine:volume of flow entering the hospital scavenging system and passing through the central collection system) since the flow rate from an anesthetic gas machine can be about 2 L/min, while the flow rate entering the hospital scavenging system can be 40 L/min. Given the dilution of anesthetics passing through the central collection system, the capture device (e.g. each canister of the central collection system specifically, or the central collection system in general) should be designed to ensure that the residence time is adequate for the adsorbent material to adsorb the anesthetics. Changing the residence time can be effected by changing the volume of the capture device or by changing the flow rate of the gas. It is appreciated that the relationship between these variables is given by the equation: Residence Time=Capture Device Volume/Gas Flow Rate.

Figure 4A:
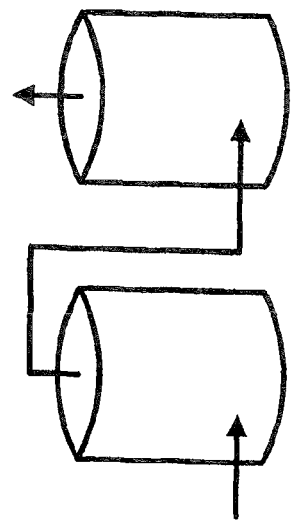
FIGS. 4a-c are schematics of contemplated embodiments of the central collection system.
Figure 4B:
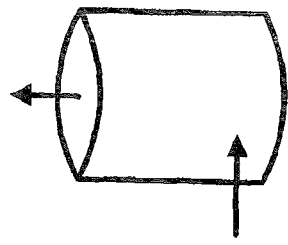
Figure 4D:
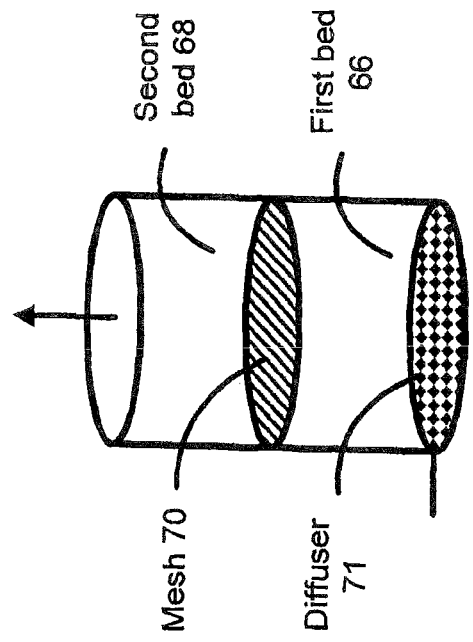
FIG. 4d is a schematic of a contemplated "layered" canister with two adsorbent layers.
Figure 4C:
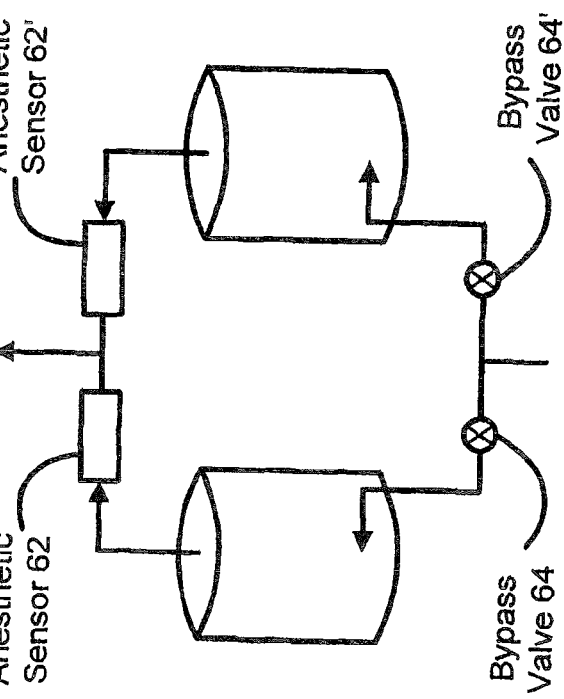

FIGS. 4a, 4b and 4c show alternative embodiments for canisters making up the collection systems described above. FIG. 4d shows one embodiment of the components which could be included in a canister. The collection system may be made up of a single canister of adsorbent (FIG. 4a), or may have multiple canisters of the same or various types of adsorbents. Canisters may be of the same or different sizes or capacities. The multiple canisters of adsorbent may be in series (FIG. 4b) or in parallel (FIG. 4c). With multiple canisters in parallel, the collection system may first pass the input gas through one or more canisters until the adsorbent in that canister (or canisters) is saturated, and then pass the input gas through another canister or set of canisters. This could be achieved by including anesthetic sensors 62 and 62' in the exhaust line of each canister to detect when anesthetic gases have broken through the adsorbent of that canister into the exhaust, and bypasses controlled by bypass valves 64 and 64' to route the input gas around that canister. Alternatively, the collection system could route the input gas away from a canister when the canister reaches a predetermined weight. In another embodiment, the collection systems may pass the input gas through all the parallel canisters at the same time.

In various cases, the canisters making up a collection system may include different adsorbent materials, and may be of different geometrical configurations, different weights and volumes, different materials of construction, and have different capacities for adsorption. The specific variables can be chosen in view of the variable concentrations of the anesthetic gas in the administered gas mixture; the variable flow rates of the administered gas mixtures; the various scavenging systems commonly used in hospitals (active or passive); the various anesthetic gas machine exhausts; the different anesthetic gas machine type of outlets; and other operating room settings. The configurations of the canisters for a particular application can be adapted to meet a hospital's requirements for the frequency of adsorber replacement, space requirements, or various other factors.

In each case, the canister can be configured to facilitate adsorbent loading and unloading, to provide proper connection to the anesthetic gas exhaust outlet; to ensure gas stream flow distribution during adsorption and regeneration; to provide easy handling; and to accommodate space availability.

A canister, a canister collection system, or a central adsorber collection system may be filled with more than one adsorbent. In such a situation, the different multiple adsorbents may be layered in separate "beds" within the single canister, as illustrated in FIG. 4d where 66 identifies a first bed, 68 identifies a second bed and 70 identifies a mesh which keeps the beds separate but allows the gas to flow from the inlet end of the canister to the outlet end of the canister. The canister illustrated in FIG. 4d also shows a diffuser 71 at the inlet end, which distributes gas throughout the canister thereby reducing the possibility that there are pockets of adsorbent which do not contact the gas stream.

Such a layered system could be used in a "staged" adsorption where the objective of each layer is to adsorb a specific target compound or compounds (e.g. the objective of the first layer would be to adsorb water, the objective of the second layer would be to selectively adsorb desflurane and isoflurane, and the objective of the third layer would be to adsorb sevoflurane). Such a layered bed could be removable from the canister for separate regeneration of the multiple adsorbents. It is appreciated that such a layered canister could be used in both the central collection system described above, as well as the container collection system described previously.

In one embodiment of a "staged" adsorption canister, the first layer contacted by the mixture of anesthetics could be a layer of adsorbent having an average pore diameter of between about 5 angstroms and about 10 angstroms. This first adsorbent would adsorb one or more anesthetics, while not adsorbing other anesthetics.

The second layer contacted by the anesthetics could be a layer of adsorbent having an average pore diameter of between about 15 angstroms and about 30 angstroms. This second adsorbent would adsorb one or more anesthetics, including, for example, sevoflurane. In such an embodiment of a "staged" adsorption canister, adsorption of a mixture of desflurane and sevoflurane could result in preferential adsorption of desflurane on the first layer and preferential adsorption of sevoflurane on the second layer.

The collection systems may have one or more in-line filter (not shown) to remove particulates and/or biological contamination before the contamination reaches the central collector. The filter can be a 0.2 micron, hydrophobic, gas cartridge filter. An example of such a filter is the High Flow TETPOR™ II pharmaceutical grade gas cartridge filter made by Domnick Hunter Limited, England.

It may be advantageous to remove specific targeted compounds from the gas flow using one or more selective adsorbents before the gas flow passes through the central collection system or container collection system. Moisture can be removed using a condenser (not shown) and/or may be removed using 3A, 4A, or other known conventional desiccants (not shown) having appropriately sized pores to avoid adsorbing the anesthetics. In order to prevent or reduce decomposition of an anesthetic caused by the desiccant, it may be desirable to first remove moisture using a condenser and then appropriately limit the amount of desiccant used to dry the gas flow and/or select a desiccant which does not result in decomposition of the anesthetic. The desiccant may be separated from the adsorbent used to adsorb the anesthetics, with the desiccant and adsorbent being located in separate canisters.

With regard to the decreased adsorption capacity of the material in the presence of water, Table 1, below, shows the breakthrough and maximum capacity of two particular halogenated anesthetics (sevoflurane and desflurane) on an adsorbent with and without water. The adsorbents were placed in lab-sized canisters, having a capacity of about 1 kg of adsorbent, which are smaller than commercially sized canisters. Breakthrough capacity of water was 127 g and the maximum capacity of water was 322 g. As can be seen, breakthrough capacities and maximum capacities of both sevoflurane and desflurane are significantly reduced in the presence of water.

TABLE 1

| Breakthrough capacity (g) | | | | Maximum Capacity (g) | | | |
|---|---|---|---|---|---|---|---|
| Sevoflurane | | Desflurane | | Sevoflurane | | Desflurane | |
| w/ $H_2O$ | w/out $H_2O$ | w/ $H_2O$ | w/out $H_2O$ | w/ $H_2O$ | w/out $H_2O$ | w/ $H_2O$ | w/out $H_2O$ |
| 188 | 378 | 113 | 234 | 300 | 542 | 210 | 369 |

According to one embodiment herein, the canister is charged with an adsorbent material having an organophillic pore lattice structure. The adsorbent can be based on $SiO_2$-based molecular sieves. Molecular sieves should be understood to be materials which contain tiny pores of a relatively precise and relatively uniform size. Materials used as an adsorbent for gases and liquids can include aluminosilicate minerals, clays, porous glasses, microporous charcoals, zeolites, active carbons, silical gel or synthetic materials.

The adsorbent can have an average pore opening of about 5 to about 50 angstroms. In particular embodiments, the adsorbent can have an average pore opening of about 5 to about 10 angstroms. In other embodiments, the adsorbent can have an average pore opening of about 15 to about 30 angstroms. It has been found that adsorbent material with an average pore size greater than 15 angstroms can be used to adsorb one or more anesthetics. Anesthetics able to be adsorbed by an adsorbent having an average pore opening greater than 15 angstroms include sevoflurane and desflurane.

Molecular sieves based on $SiO_2$ typically have a formula of $M_x(Al_2O_3)_y(SiO_2)_z$ where M is a cation. It is preferable to avoid adsorbent materials with a basic surface as some halogenated hydrocarbons can be degraded under basic (i.e. high pH) conditions. Since $Al_2O_3$ is basic in character (typically existing as $Al(OH)_4^-$ under neutral conditions), adsorbents contemplated in the present application preferably have less than about 10% by total weight of $Al_2O_3$. More preferably, the adsorbent used in the present application has less than 5% by total weight of $Al_2O_3$. An adsorbent which is substantially free of $Al_2O_3$ is particularly preferable. It would be understood that an adsorbent which is "substantially free of $Al_2O_3$" is an adsorbent which has no more than about 1% w/w of $Al_2O_3$.

Adsorbent material with a neutral surface (i.e. with low levels of cations in the lattice) is preferable, since cations (such as $Na^+$, $K^+$, $Ca^{2+}$, $Al^{3+}$ etc) may cause catalytic reactions and degradation of the halogenated hydrocarbon being adsorbed. An adsorbent material with a neutral surface would be understood to mean an adsorbent having less than 1%, preferably less than 0.1% and particularly preferably less than 0.01%, by mass, of cation.

It would be understood that changes in pore size and active surface area of the material would affect the total amount of halogenated hydrocarbon which could be adsorbed. Adsorbent having a specific surface area of about 400 $m^2/g$ to about 1500 $m^2/g$ could be used. According to one embodiment, the adsorbent is an amorphous silica adsorbent that has an average pore size of about 20 angstroms, a specific surface area of about 750 $m^2/g$, a pore volume of about 0.4 mL/g and has less than about 1.0 wt % $Al_2O_3$.

The canister can be charged with an additional adsorbent material that has a pore lattice structure with an average pore opening of between about 5 and about 10 angstroms. This additional adsorbent material can be used to adsorb one or more anesthetics. One anesthetic which is able to be adsorbed by the additional adsorbent material is desflurane. Using the additional adsorbent material would allow selective adsorption of desflurane from a mixture of desflurane and sevoflurane.

According to one embodiment, the additional adsorbent material is a silica adsorbent that has average pore size of about 6 angstroms, a specific surface area of about 400 m$^2$/g, a pore volume of about 0.14 mL/g, and has less than about 1.0 wt % $Al_2O_3$.

In one embodiment, the canister, which may be cylindrical in shape, has an inlet located at or near the bottom and an outlet at the other end. The inlet can be attached via a pipe to a diffuser at the bottom of the canister, as illustrated in FIG. 4d. Alternatively, the inlet and an outlet can both be located at the same end. The canister could be made from any material with appropriate heat resistant and corrosion resistant properties. The material could be, for example, ceramic, glass, engineered plastic or stainless steel, such as SS316.

The gas stream in discharge line 26 exiting the anesthetic gas machine 18 (see FIG. 1) typically contains moisture. This has presented significant problems in the past in attempting to recover anesthetics from gas stream exiting anesthetic gas machines. In order to overcome this problem, the moist gas stream may be first passed through a hydroscopic adsorbent which adsorbs the moisture, but has pore sizes that avoid the adsorption of anesthetic. In this manner, the moist gas stream can be dried prior to capture of the anesthetic on the adsorbent. It is would be readily understood that the hydroscopic adsorbent could be placed inside or outside the canister, as long as it was in-line with the anesthetic adsorbent and adsorbed the moisture before the gas stream passed through the anesthetic adsorbent.

A single patient is usually treated with a single anesthetic. However, during the time that a container collection system or a breathing circuit collection system is attached to an individual anesthetic gas machine, several different operations may occur with different anesthetics being used. Additionally, in a central adsorber collection system, each anesthetic gas machine in each operating room of a hospital may be using different anesthetics. In either of the above situations, a canister of adsorbent in either of (i) a central adsorber collection system or (ii) an canister collection system would be exposed to several anesthetics, in sequence or simultaneously. Different anesthetics may have different effects on the anesthetic adsorbents. It is believed that the adsorption of an anesthetic results in heat generated during the adsorption process. It is therefore sometimes desirable to first capture one or more specific anesthetics using a first anesthetic adsorbent before capturing one or more other anesthetics. In a similar manner, it may be desirable to remove as much water as possible before adsorbing the inhalation anesthetic in order limit the heat released during the adsorption process.

Figure 5:
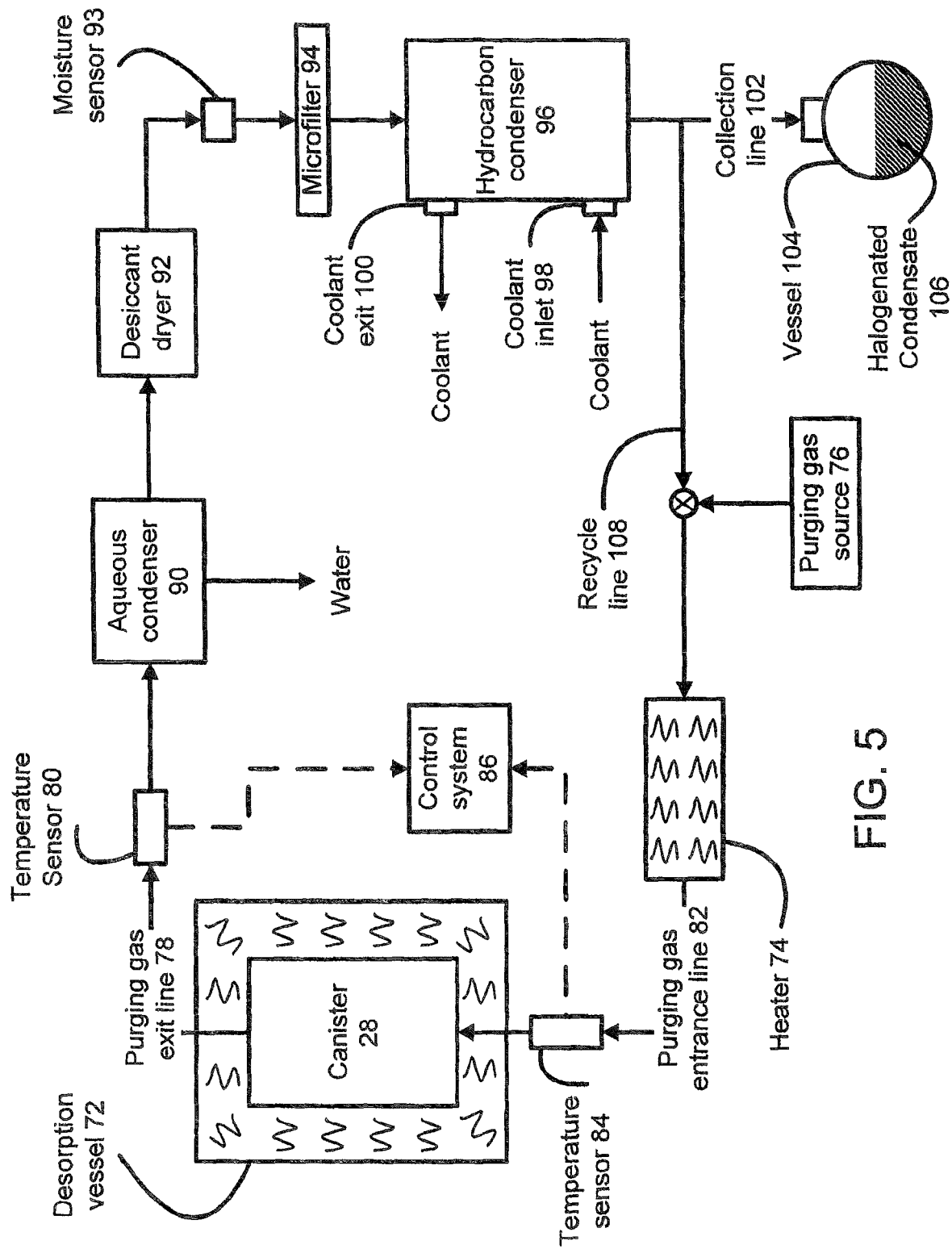
FIG. 5 is a schematic of a system used to regenerate the adsorbed material in a canister and recover the captured material.

Canisters loaded with adsorbed anesthetics can be subjected to a process to regenerate the anesthetic adsorbent in the canister 28 and to recover the anesthetic material. An embodiment of a general desorption system is illustrated in FIG. 5. A desorption system could process a single canister at a time or multiple canisters in series or in parallel. A desorption system could be integrated with a central collection system so that the adsorbent of the central collection system could be regenerated without having to be removed from the central collection system.

In the system of FIG. 5, the canister may be heated within a desorption vessel 72, to enhance the desorption of the adsorbed anesthetics. In one example, the adsorbents are heated to a temperature range of about 25° C. to about 220° C. Preferably, the desired temperature is between 60° C. and 120° C. It is appreciated that with different types of halogenated hydrocarbons, different temperature ranges may be necessary to desorb the compounds. In order to heat the adsorbents within the canister to the desired temperature, the desorption vessel 72 may be a conventional oven having heating coils surrounded by insulating material. It is understood that in view of the transparency of the anesthetic adsorbing material to microwaves, a microwave oven may be substituted for the conventional oven.

While FIG. 5 shows one canister, it should be appreciated that the desorption process could be run with more than one canister (not shown) connected in parallel or in series.

A purging gas is passed through the canister 28 to desorb the organic anesthetics from the adsorbent or adsorbents. In accordance with a particular aspect of this application, the purging gas is an inert gas. The inert purging gas can be nitrogen. In one arrangement, the canister or canisters are not contained within a heated desorption vessel 72 (such as a conventional or microwave oven) but heat for desorbing the anesthetics can come from heated purging gas.

The purging gas may be heated using a heater 74. As noted above, in some cases, the adsorbents in canister 28 may be heated by heating the nitrogen gas or air purging stream, even if direct application of heat to the canister is not applied. In accordance with the embodiment illustrated in FIG. 4, nitrogen gas is heated in heater 74 to the desired temperature in the range of about 25° C. to about 220° C. Preferably, the desired temperature is between about 60° C. and about 120° C. FIG. 4 shows the desorption system as a closed loop, the purging gas being continuously recycled. Any loss of purging gas from the system (e.g. due to removal of material from the system) can be replenished via purging gas source 76.

It may be desirable to desorb canister 28 at a higher temperature, for example if removal of water is desired, typically after the anesthetics have already been desorbed. In such a situation, canister 28 and/or the purging gas stream can be heated to about 200° C. or higher. It may even be desirable to heat the canister 28 and/or the purging gas stream to as high as 1000° C. in order to more thoroughly regenerate the canister.

It is appreciated that temperature and pressure both affect the amount of time required to regenerate the adsorbent. Increasing the temperature and/or decreasing the pressure reduce the amount of time required for desorption, while decreasing the temperature and/or increasing the pressure would increase the amount of time required for desorption.

In some situations, it may be desirable to desorb the canister under a partial vacuum since the reduced pressure would reduce the temperature required to regenerate the adsorbent, and thereby reduce decomposition of any temperature sensitive adsorbed anesthetics. In an embodiment where the desorption process is operated under vacuum, the adsorbents may be heated to 50° C. to effect desorption of the anesthetics. In an embodiment at standard pressure, the adsorbents may be heated to about 120° C. to effect desorption of the anesthetics. It is believed that at a reduced pressure, the canister 28 could be regenerated at temperatures between about 50° C. and about 60° C. Regeneration of adsorbent could also be achieved at temperatures as low as 25° C., where the time for regeneration is thereby extended.

The purging gas passes through the adsorbents in the canister 28. The purging gas exits the canister 28 through purging gas exit line 78 and may pass through a temperature sensor 80. The temperature sensor 80 provides an indication of the temperature of the purging gas in the exit line 78. When the temperature of the purging gas in the exit line 78 achieves a temperature nearing that of the temperature in purging gas entrance line 82, it can be determined that the adsorbents are at a temperature approximating the inlet temperature and that most of the anesthetics have been desorbed. The system is then run for a desired period of time beyond that point to ensure complete desorption. Alternatively, the purging gas can be run for a predetermined time, with the predetermined time being based on empirical knowledge gained from historical desorption experiments. In another alternative, a sensor can be used to determine the presence of anesthetic in the exit line.

The desorption process may be automated and a temperature sensor 84 may be included in the inlet side to measure the temperature of the incoming stream. By way of a suitable microprocessor, the signals from the temperature sensors 80 and 84 may be fed to a control system 86 which compares the temperatures and actuates a signal to indicate that canister regeneration process is complete. It is appreciated that regeneration of the adsorbents may take place at lower temperatures outside of the preferred range.

It is appreciated that, adsorbents may be removed from their canister and placed with adsorbents removed from other canisters. The combined adsorbents may then be regenerated in a separate vessel in a manner as discussed above with respect to a single canister.

The stream of purging gas coming from the canister via the purging gas exit line 78 can optionally be passed through an aqueous condenser 90 to remove water from the gas stream. This aqueous condenser 90 can be operated at a temperature of, for example, 0° C. to 20° C. The gas stream can then be optionally passed through a desiccant dryer 92 to remove any residual water. The desiccant dryer 92 could, preferably, remove sufficient moisture to lower the dew point to below about −60° C. The moisture content (i.e. dew point) could be measured, for example, with moisture sensor 93. The dessicant dryer 92 could include multiple containers of dessicant and the gas stream could be directed through the containers in series and/or in parallel, in a similar manner as discussed with regard to the canisters of adsorbent illustrated in FIG. 4*a-c*.

The gas stream can also be passed through a microfilter 94 to remove any particulates and/or biological contamination. In one embodiment, the filter is a 0.2 micron, hydrophobic, gas cartridge filter. An example of such a filter is the High Flow TETPOR™ II pharmaceutical grade gas cartridge filter made by Domnick Hunter Limited, England. Finally, the gas stream can be passed through hydrocarbon condenser 96. The purpose of the hydrocarbon condenser 96 is to remove, in liquid form, the anesthetic from the purge gas. The hydrocarbon condenser 96 can be cooled with an appropriate coolant (such as liquid nitrogen, silicone oil cooled by dry ice, or gaseous nitrogen at cryogenic temperature), which can be fed through the hydrocarbon condenser 96 via coolant inlet 98 and coolant exit 100. This provides sufficiently cool temperatures in the hydrocarbon condenser 96 to cause the anesthetics to condense and collect, via connection line 102, in vessel 104 as halogenated condensate 106. The hydrocarbon condenser 96 can be operated at a condensing temperature between about −20 and about −100° C. In particular embodiments, the hydrocarbon condenser 96 can be operated at a condensing temperature between −20 and −65° C. The gas stream can be recycled to the heater 74 via recycle line 108. A sensor capable of detecting anesthetic could also be used to adjust the conditions at the hydrocarbon condenser 96.

It would be appreciated that any of the noted elements (e.g. desiccant 92, microfilter 94 or the like) could be doubled, tripled, quadrupled, or otherwise and could be attached in serial or in parallel as a way of introducing redundancy and continuous operation into the system. In the situation where elements are arranged in parallel it may be advantageous to include a sensor or timer to shift between parallel streams. For example, where there are multiple desiccant dryers 92, it may be advantageous to also include a moisture sensor 93 which could detect moisture in the gas stream exiting the first desiccant dryer 92 and switch the gas stream to a second desiccant dryer arranged in parallel. One example of moisture sensor 93 is a dew point monitor.

As discussed above, a mixture of anesthetics may be adsorbed by the anesthetic adsorbing material. Hence, the halogenated condensate collected from the desorption process may consist of a mixture of anesthetics and may also include additional decomposition products and other compounds or impurities. Regardless of the composition of the halogenated condensate, the individual anesthetics are preferably separated, isolated and purified to predetermined standards, which may include medical standards at which the recovered anesthetics can be administered to patients. The medical standards for each anesthetic have a regulated purity level, normally in excess of 95 wt %, with the remaining impurities also having specified limits. An alternative predetermined standard may be to provide a level of purity that could then conveniently be subject to additional processing to reach the medical standard. For example, the anesthetics could be provided in a form suitable to be a raw material for subsequent processing.

To achieve the desired purity, the halogenated condensate can be subjected to fractional distillation. It is understood that it would be possible to operate a distillation process as either a batch or continuous process. It is appreciated that a single column of appropriate length could be used to purify all the anesthetics, or that a multi-column system could be used. It is also appreciated that distillation could be used to purify only a single anesthetic (such as desflurane, sevoflurane or isoflurane) while leaving the remaining anesthetics in the halogenated condensate. In this manner, the halogenated condensate could be enriched with one or more of the anesthetics.

Figure 6A:
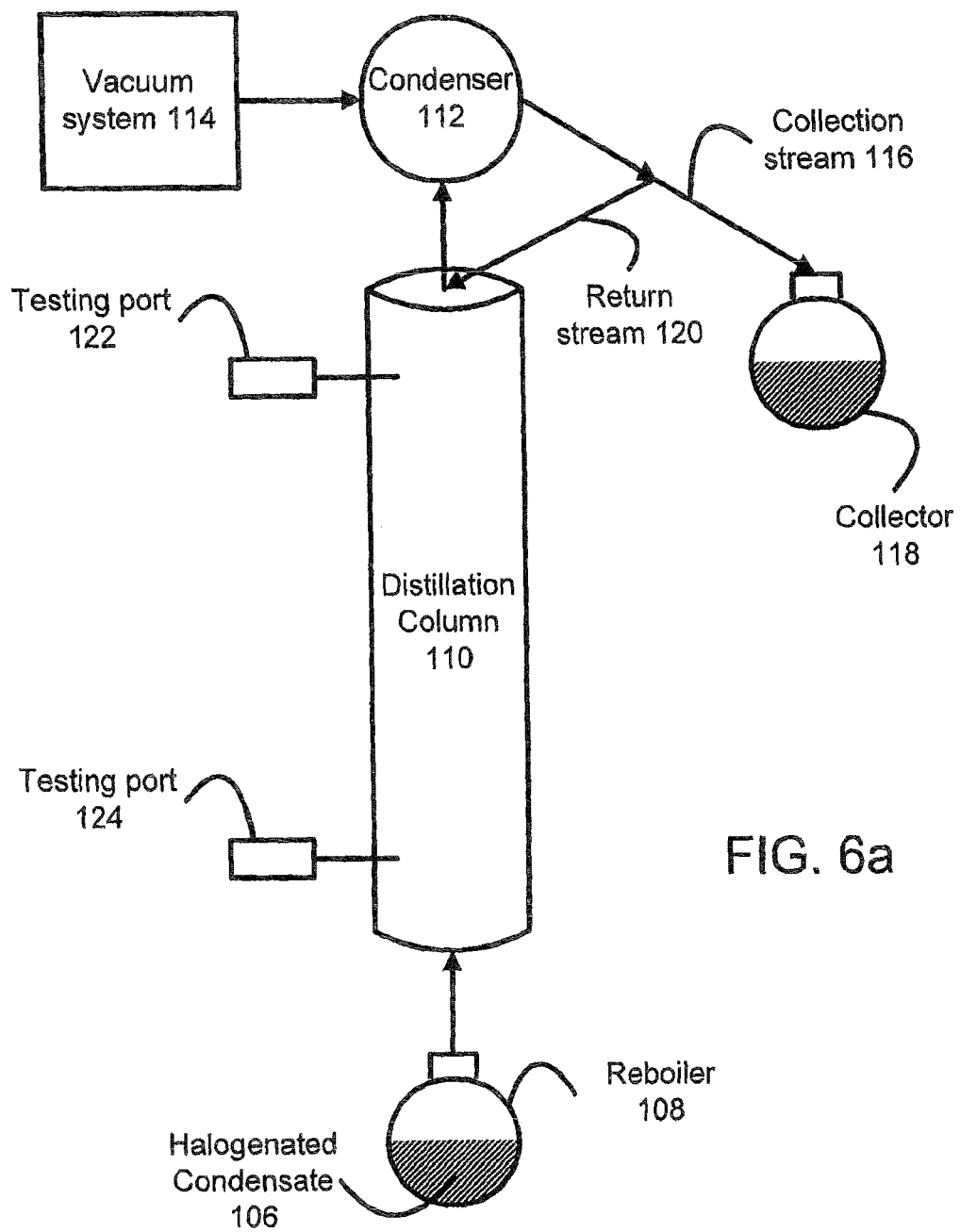
FIG. 6a is a schematic of a single column, batch distillation apparatus for purifying the components of the captured material.

An embodiment of a distillation system with a single column, used for a batch process, is illustrated in FIG. 6*a*. Halogenated condensate is heated in reboiler 108 and fed to column 110. The vapors in column 110 are condensed in condenser 112. A vacuum system 114 at the top of the column 110 could allow the distillation process to be performed under a partial vacuum. The condensed liquid exiting the condenser 112 is split into two streams: collection stream 116, which is purified liquid collected in collector 118; and return stream 120, which is a stream that re-enters the distillation column 110. The ratio between the collection stream 116 and the return stream 120 is termed the "reflux ratio". A properly chosen reflux ratio aids in achieving the desired purity.

The distillation system illustrated in FIG. 6*a* could also include one or more testing points along the column, such as via testing ports 122 and 124, which could be used to test the temperature and composition of the vapors in the column during distillation. The temperature and/or the composition of the vapors could be used to set the reflux ratio and/or the amount of energy used to heat the reboiler 108.

Figure 6B:
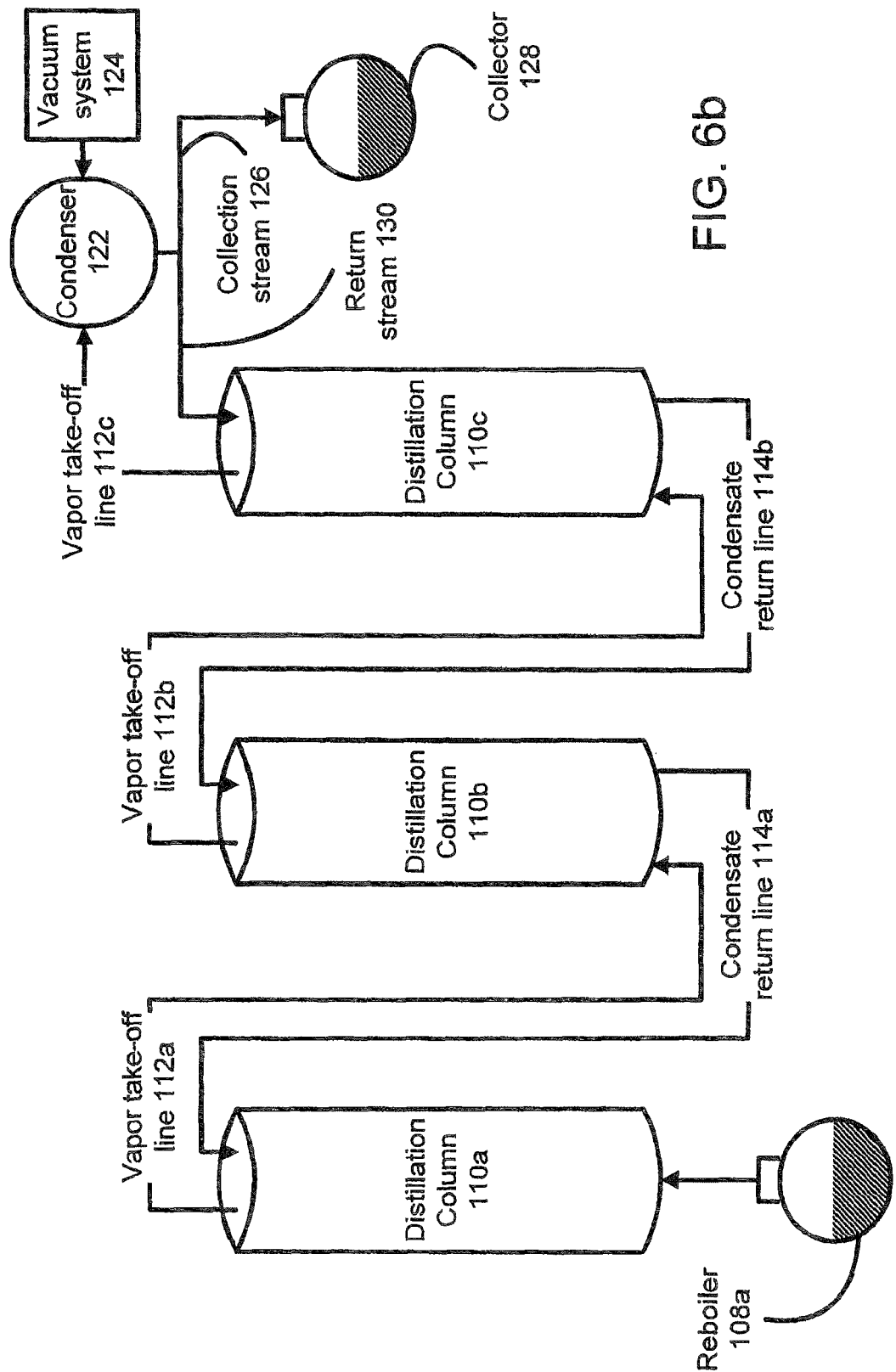
FIG. 6b is a schematic of a multi-column, batch distillation apparatus for purifying the components of the captured material.

Another system is a multi-column, batch distillation system, an example of which is illustrated in FIG. 6b. This system consists of a multistage fractional distillation system having three distillation columns 110a, 110b and 110c. The halogenated condensate is heated in reboiler 108a and rises into column 110a. Sufficient energy is applied to reboiler 108a to cause the liquid to boil and provide a vapor take-off in vapor take-off line 112a. The vapor in line 112a is fed to the bottom of column 110b. Condensate from the bottom of the column 110b is fed back into the top of column 110a via condensate return line 114a. In a similar manner, the vapor in vapor take-off line 112b is fed to the bottom of column 110c. Condensate from the bottom of column 110c is fed back into the top of column 110b via condensate return line 114b. The vapor in vapor take-off line 112c can be condensed in condenser 122. A vacuum system 124 at the top of the distillation column 110c can allow the distillation process to be performed under a partial vacuum. The condensed liquid exiting the condenser 122 is split into two streams: collection stream 126, which is a purified liquid collected in collector 128; and return stream 130, which is a stream that re-enters the distillation column 110c. As discussed above, the ratio between collection stream 126 and the return stream 130 is termed the "reflux ratio". A properly chosen reflux ratio aids in achieving the desired purity.

It will be appreciated that any of the contemplated distillation systems may be operated at atmospheric pressure or under a partial vacuum or under pressure. Additionally, the contemplated distillation systems could have in-line analysis capability to determine the temperature and composition of the liquid and/or vapor phase at any point along the column. This in-line analysis capability could be connected to a computer controlled automatic feedback system which could control the amount of heat applied to the reboiler, the pressure in the column, and/or the reflux ratio in order to regulate the distillation process.

The contemplated distillation columns may be packed with an appropriate packing to increase the internal surface area of the column and increase the number of theoretical plates per unit length of column. Examples of an appropriate packing material could include metal, ceramic or glass.

The reboiler of the contemplated batch distillation systems may be operated at a first setting in order to process a first component of a mixture before being operated at a second setting in order to process a second component of the mixture. The reboiler(s) may be operated between about 500 kW and about 1500 kW, but the actual setting is a function of the quantity and composition of the material in the reboiler, including, for example, the reflux ratio.

In one particular embodiment of a multi-column, batch distillation system used for proof of concept and interim processing, distillation column 1 can be 190" in length and 3" in outside diameter. Distillation column 2 can be 202" in length and 3" in outside diameter. Distillation column 3 can be 166" in length and 3" in outside diameter. In another particular embodiment, distillation column 1 can be 166" in length and 3" in outside diameter. Distillation column 2 can be 176" in length and 3" in outside diameter. Distillation column 3 can be 115" in length and 3" in outside diameter. The packing material in the columns can be a 0.24 inch protruded metal ribbon, with a surface area of 372 square feet per cubic foot. Such a packing material can have a packing factor of 420. One example of such a packing material is 0.24-Inch Pro-Pak Protruded Packing.

Within a mixture of anesthetics, a number of impurities can also be present. These impurities may include chloromethane; 2,2,2-trifluroethanol; chloromethyl 2,2,2-trifluoromethyl-ethyl ether; 1,1,1,3,3,3-hexafluoroisopropanol; $[(CF_3)_2CHO]_2=CH_2$; and/or $(CF_3)_2CHOCH_2OCH_2CF_3$. Such impurities may result in azeotropic mixtures with one or more of the anesthetics, resulting in reduced effective yields during distillation. In a situation where impurities are present, it may be desirable to reduce the amount of or remove the impurities from the halogenated condensate before distillation is performed. As one example, the halogenated condensate may be washed with water, preferably in about a 1:2 wt/wt ratio. The water washing may be repeated until desired specifications (for example, a desired reduction in the amount of impurities) are met. In the situation where 1,1,1,3,3,3-hexafluoroisopropanol is present, it may be desirable to wash with water until the level of 1,1,1,3,3,3-hexafluoroisopropanol is less than about 1.5% wt/wt, and preferably less than 0.1% wt/wt. The level of 1,1,1,3,3,3-hexafluoroisopropanol may be analyzed by gas chromatography or other suitable analytical technique.

Without limiting the scope of the present application, the following examples exemplify aspects of and information relating to the embodiments herein. The following examples were performed in laboratory situations using experimental canisters. It will be understood that the experimental canisters may be smaller than commercially sized canisters.

Example 1

Figure 7:
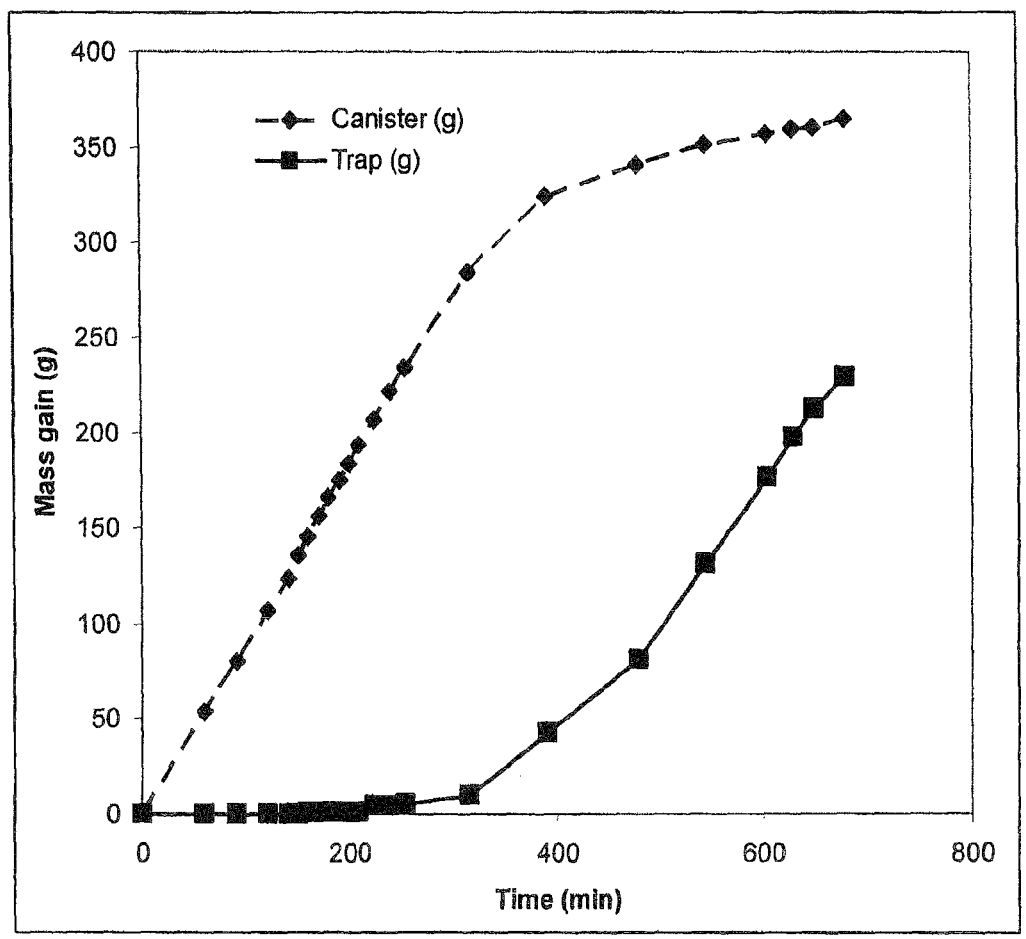
FIG. 7 illustrates the mass change over time of a canister and a trap, each filled with an adsorbent and having desflurane passed therethrough.

The breakthrough and maximum adsorption capacities of an adsorbent was determined for desflurane and sevoflurane. A canister was filled with about 1,100 grams of an adsorbent. The adsorbent was an amorphous silica adsorbent with an average pore size of about 20 angstroms, a specific surface area of about 750 $m^2/g$, and less than about 1.0 wt % $Al_2O_3$. Desflurane at a concentration of 6% by volume, in nitrogen was passed through the canister at a rate of 2 liters per minute. The outlet gas was passed through a second canister (the "trap") having the same adsorbent as the first canister. FIG. 7 shows the mass changes of the canister and trap over time. It can be seen that the breakthrough capacity of the canister is about 234 g of desflurane, while the maximum capacity is 369 g of desflurane. In this case, breakthrough is deemed to be the point when the weight gain in the trap exceeds 5 grams.

Figure 8:
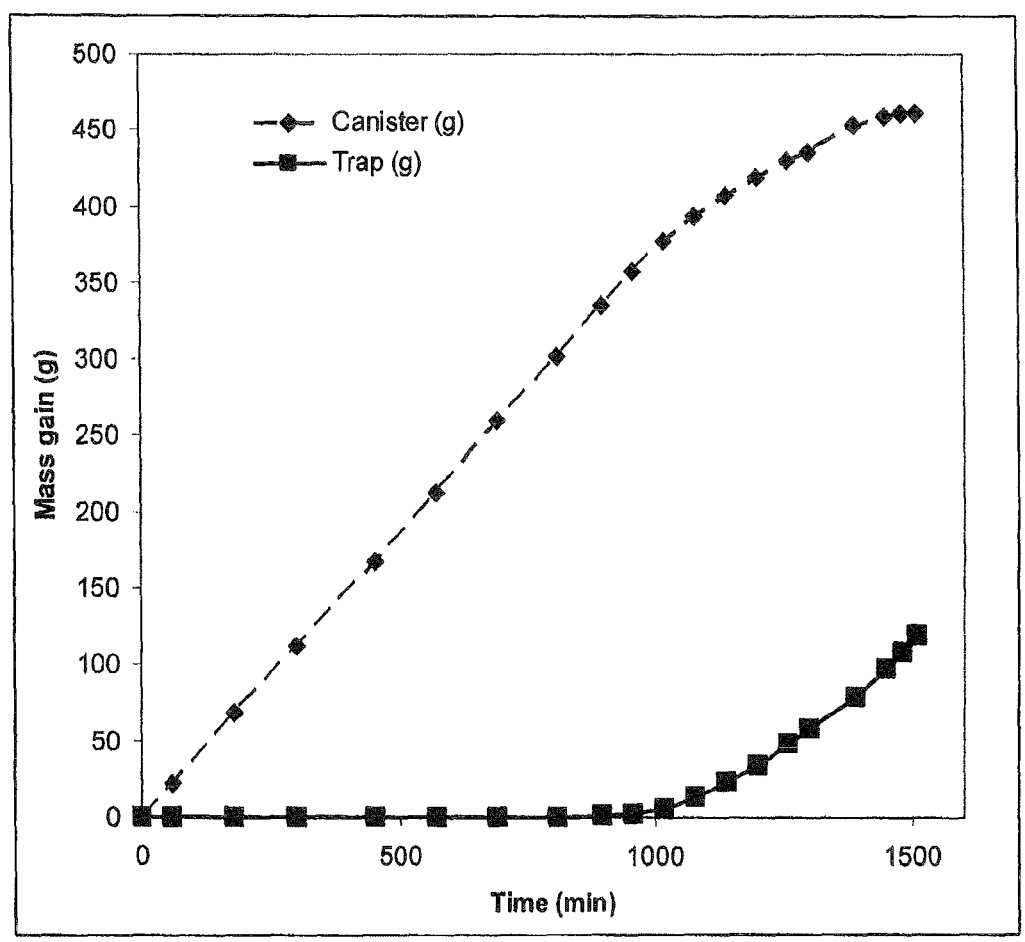
FIG. 8 illustrates the mass change over time of a canister and a trap, each filled with an adsorbent and having sevoflurane passed therethrough.

In a similar experiment, sevoflurane, at a concentration of 2% by volume in nitrogen, was passed through a canister of 1,100 g of adsorbent at a rate of 2 liters per minute. The outlet gas was passed through a trap having the same adsorbent as the canister. FIG. 8 shows the mass changes of the canister and trap over time. It can be seen that the breakthrough capacity of the canister is 378 g of sevoflurane, while the maximum capacity is 461 g of sevoflurane.

Example 2

Figure 9:
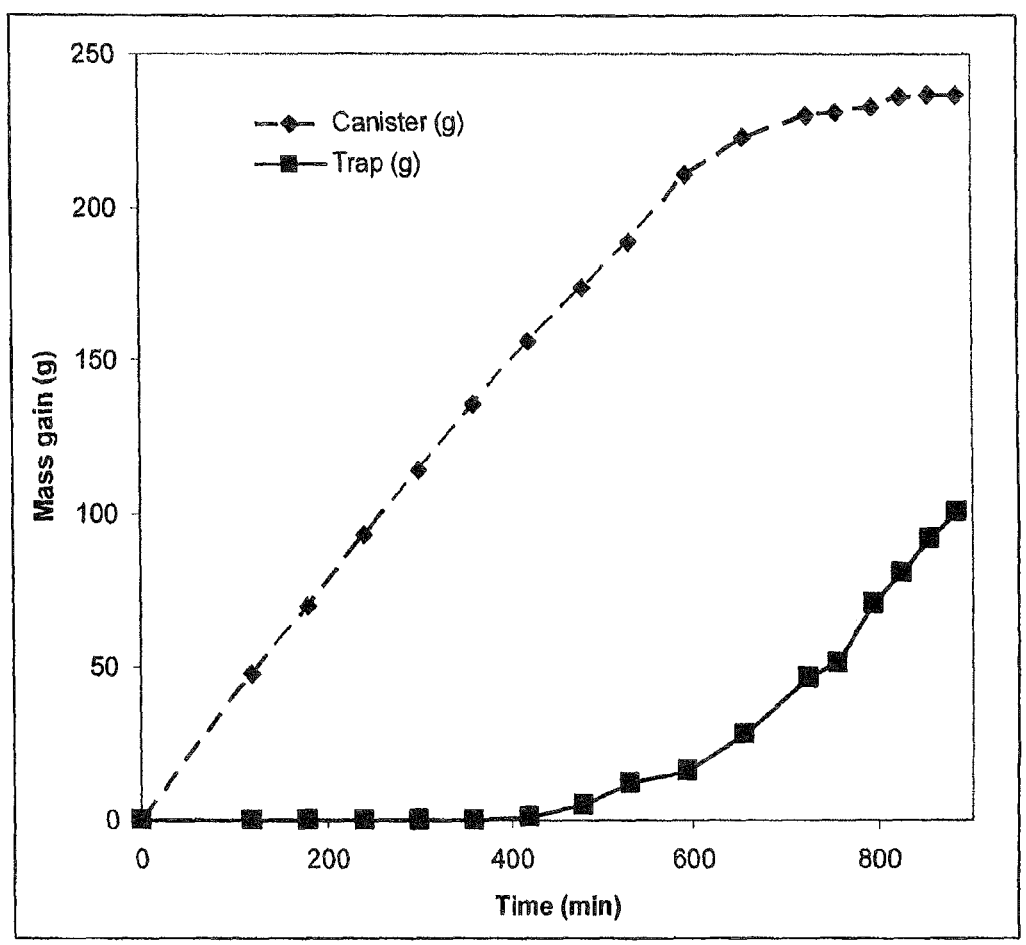
FIG. 9 illustrates the mass change over time of a canister and a trap, each filled with two adsorbents and having sevoflurane passed therethrough.

The breakthrough and maximum adsorption capacities of a canister containing layers of two adsorbents was determined for sevoflurane. A canister was provided with about 550 grams of a first adsorbent and about 550 grams of a second adsorbent. The two adsorbents were kept separated and not mixed. Gas passing through the canister would first contact the first adsorbent and then contact the second adsorbent. The first adsorbent was a silica adsorbent with an average pore size of about 6 angstroms, a specific surface area of about 400 m²/g, and less than about 1.0 wt % $Al_2O_3$. The second adsorbent was an amorphous silica adsorbent with an average pore size of about 20 angstroms, a specific surface area of about 750 m²/g, and less than about 1.0 wt % $Al_2O_3$. FIG. 9 shows the mass changes of the canister and trap over time. It can be seen that the breakthrough capacity of the canister is 172 g of sevoflurane, while the maximum capacity is 237 g of sevoflurane.

Example 3

Multi-canister setups were evaluated for optimization of the collection of anesthetics. In this procedure, two canisters of adsorbent were placed in series and subjected to routines that would likely be carried out in a normal operating room. Table 2 describes the routines for each "day" in the operating room. Each loading period was separated by a 5 minute purge of 10 L/min of nitrogen gas. Furthermore, an "idle" period of 30 minutes after every post-operation purge was included, which represented the inactive period between operations.

TABLE 2

| | | Total loading (h) | |
|---|---|---|---|
| Day | Case Description | Sevoflurane | Desflurane |
| 1 | Load with 2% sevoflurane for 2 hours, repeat 3 times. | 6 | 0 |
| 2 | Load with 2% sevoflurane for 2 hours, repeat 2 times. Load with 6% desflurane for 1 hours, repeat 2 times. | 4 | 2 |
| 3 | Load with 2% sevoflurane for 1 hours, repeat 3 times. Load with 6% desflurane for 1 hours, repeat 3 times. | 3 | 3 |
| 4 | Load with 2% sevoflurane for 1 hours, repeat 2 times. Load with 6% desflurane for 2 hours, repeat 2 times. | 2 | 4 |
| 5 | Load with 6% desflurane for 2 hours, repeat 3 times. | 0 | 6 |

A trap was placed in series after the two canisters. The trap was also monitored for changes in weight. Table 3 shows the weight changes of the three canisters at the end of each "day".

TABLE 3

| | Weight gain (grams) | | | |
|---|---|---|---|---|
| Day | Canister 1 | Canister 2 | Cumulative | Trap |
| 1 | 151 | 1 | 152 | 0 |
| 2 | 349 | 20 | 369 | -2 |
| 3 | 377 | 235 | 612 | 3 |
| 4 | 365 | 372 | 737 | 123 |
| 5 | 353 | 419 | 772 | 174 |

In comparison, a 1-canister system was evaluated using a similar setup. Using a 1-canister system, 353 grams of anesthetics were adsorbed. It would be expected that a 2-canister system would adsorb twice as much, or 706 grams. Since 772 grams of anesthetics were actually adsorbed using a 2-canister system, a surprising additional 66 grams were adsorbed when the two canister were placed in series. Given that the total amount of anesthetic used in these procedures was 946 grams, the additional 66 grams represents an additional collection of about 7%. It is believed that the first canister is driven to a maximum since it continues to be exposed to anesthetic while the second canister is also collecting anesthetics.

Example 4

The effect of the adsorbent composition on sevoflurane was evaluated by adsorbing sevoflurane on a variety of adsorbents. The various adsorbents had varying compositions of $SiO_2$ and $Al_2O_3$. Table 4 shows five silica gel and zeolite adsorbents, with amounts of $Al_2O_3$ ranging from 20 wt % to <0.5 wt %. About 100 grams of sevoflurane was adsorbed onto the adsorbents and then subsequently desorbed for 4 hours using nitrogen at temperatures between 95° C. and 130° C. The composition of the resulting desorbed mixture was determined by gas chromatography. Table 4 shows that adsorption of sevoflurane increases and decomposition of sevoflurane decreases as the amount of $Al_2O_3$ in the adsorbent decreases.

TABLE 4

| Adsorbent | #100 | #200 | #300 | #400 | #500 |
|---|---|---|---|---|---|
| $Al_2O_3$ (wt %) | 20 | 15-20 | 15 | 3 | <0.5% |
| GC Analysis (%) | | | | | |
| sevoflurane | 0.2 | 38.6 | 97.68 | 99.93 | 99.78 |
| 1,1,1,3,3,3-hexafluoroisopropanol | 3.6 | 47.1 | 2.23 | 0.06 | 0.02 |
| Others | 96.2 | 14.3 | 0.09 | 0.01 | 0.2 |

In the preceding description, for purposes of explanation, numerous details are set forth in order to provide a thorough understanding of the embodiments. However, it will be apparent to one skilled in the art that other arrangements and embodiments would be feasible.

The above-described embodiments are intended to be examples only. Alterations, modifications and variations can be effected to the particular embodiments by those of skill in the art without departing from the scope of the application, which is defined solely by the claims appended hereto.

The invention claimed is:

1. A conservation valve for use with a collection system for collecting an anaesthetic agent, the conservation valve comprising:
   a valve body having an inlet port, an outlet port, and a fluid passageway between the inlet port and the outlet port, the inlet port connectable to a source of exhaust gas so as to allow the exhaust gas to flow through the fluid passageway, and the outlet port connectable to the collection system;
   a sensor located upstream of the valve body for detecting a percentage content of anaesthetic agent within the exhaust gas, the percentage content of the anaesthetic agent being indicative of the level of anaesthetic agent being present within the exhaust gas;
   wherein the sensor generates an electrical signal to operate the valve body to
      close the fluid passageway when the percentage content of the anaesthetic agent is below a predetermined level to isolate the exhaust gas from the collection system, wherein the anaesthetic agent is a halogenated hydrocarbon.

2. The conservation valve of claim 1 wherein the sensor comprises:

an electrical current generator for passing a current through the gas stream;
a conductivity sensor for determining the thermal conductivity of the gas stream based on the current passing through the gas stream;
a processor for comparing the thermal conductivity with predetermined values to determine if halogenated hydrocarbons are present in the gas stream.

* * * * *